(12) United States Patent
Levasseur, Jr. et al.

(10) Patent No.: US 8,861,813 B2
(45) Date of Patent: Oct. 14, 2014

(54) MULTI-FUNCTION, FOOT-ACTIVATED CONTROLLER FOR IMAGING SYSTEM

(75) Inventors: Donald P. Levasseur, Jr., Lititz, PA (US); Steven R. Cox, Cincinnati, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 185 days.

(21) Appl. No.: 12/921,785

(22) PCT Filed: Mar. 5, 2009

(86) PCT No.: PCT/US2009/036094
§ 371 (c)(1),
(2), (4) Date: Sep. 10, 2010

(87) PCT Pub. No.: WO2009/114365
PCT Pub. Date: Sep. 17, 2009

(65) Prior Publication Data
US 2011/0044519 A1    Feb. 24, 2011

Related U.S. Application Data

(60) Provisional application No. 61/036,148, filed on Mar. 13, 2008.

(51) Int. Cl.
| | | |
|---|---|---|
| G06K 9/00 | (2006.01) | |
| A61B 6/04 | (2006.01) | |
| A61B 6/00 | (2006.01) | |
| A61G 13/02 | (2006.01) | |
| G06F 19/00 | (2011.01) | |

(52) U.S. Cl.
CPC ............... *A61B 6/467* (2013.01); *A61G 13/02* (2013.01); *G06F 19/3412* (2013.01); *A61B 6/0457* (2013.01)

USPC ........................................... 382/128; 382/100

(58) Field of Classification Search
USPC ................................. 382/128–132
See application file for complete search history.

(56) References Cited

U.S. PATENT DOCUMENTS

| | | | | |
|---|---|---|---|---|
| 3,862,426 A | * | 1/1975 | Thomas | 378/91 |
| 5,322,084 A | * | 6/1994 | Ghiassian | 137/607 |
| 5,883,615 A | * | 3/1999 | Fago et al. | 345/156 |
| 6,051,797 A | * | 4/2000 | Meinel | 200/86.5 |
| 6,801,594 B1 | * | 10/2004 | Ali et al. | 378/4 |
| 7,331,711 B2 | * | 2/2008 | Sandkamp et al. | 378/197 |
| 7,809,111 B2 | * | 10/2010 | Meer et al. | 378/114 |
| 2004/0076259 A1 | * | 4/2004 | Jensen et al. | 378/91 |
| 2007/0269011 A1 | * | 11/2007 | Sandkamp et al. | 378/114 |
| 2008/0030192 A1 | * | 2/2008 | Fukui et al. | 324/308 |
| 2008/0253519 A1 | * | 10/2008 | Bonfiglio et al. | 378/65 |

* cited by examiner

*Primary Examiner* — Avinash J Yentrapati
(74) *Attorney, Agent, or Firm* — James L. Johnson; Marsh Fischmann & Breyfogle LLP (57) ABSTRACT

A foot-activated controller (70) for an imaging system (10) is disclosed. The foot-activated controller (70) may include a first controller section (80) and a second controller section (90) that may be disposed in each of a joined or separated state or configuration. The first controller section (80) may incorporate one or more first actuators (86) that are dedicated to communicating with one or more components that provide an imaging functionality (e.g., an imaging assembly (12)), while the second controller section (90) may incorporate one or more second actuators (96) that are dedicated to communicating with one or more components that provide a physical positioning functionality (e.g., a table positioner 38, where the table positioner (38) may be activated to control/establish the position of a table (32) on which a patient may be positioned for performance of one or more medical procedures (e.g., urology)).

29 Claims, 6 Drawing Sheets

MULTI-FUNCTION, FOOT-ACTIVATED CONTROLLER FOR IMAGING SYSTEM

RELATED APPLICATIONS

This patent application is a U.S. National Stage of PCT/US2009/036094 filed on 5 Mar. 2009, which claims priority to and is a non-provisional application of U.S. provisional application Ser. No. 61/036,148 filed on 13 Mar. 2008 and entitled "MULTI-FUNCTION, FOOT-ACTIVATED CONTROLLER FOR IMAGING SYSTEM."

FIELD OF THE INVENTION

The present invention generally relates to the field of imaging systems that utilize imaging equipment and a movable table and, more particularly, to foot-activated controllers for such imaging systems.

BACKGROUND

Medical imaging systems exist that utilize an adjustable patient table and appropriate imaging equipment. One such imaging system is commonly referred to as a "urology table." Urology tables are used to perform various urology procedures. It is common for these types of medical imaging systems to utilize foot-activated controllers for communicating with the movable patient table and the imaging equipment. One foot-activated controller is typically provided for communicating with the movable patient table, while a separate foot-activated controller is typically provided for communicating with the imaging equipment.

Known foot-activated controllers for the patient table incorporate a number of pedals or switches for controlling the position of the patient table. Patient tables for urology applications typically are movable in each of a vertical dimension, as well as longitudinal and lateral dimensions within a reference plane that at least generally coincides with a supporting surface of the patient table. These tables may also be tilted about a horizontal axis (e.g., to raise the patient's head and simultaneously lower the patient's feet; to lower the patient's head and simultaneously raise the patient's feet). Known foot-activated controllers for the imaging equipment incorporate a number of pedals or switches for controlling various aspects of the image acquisition function.

SUMMARY

A first aspect of the present invention is embodied by an imaging system. Components of this imaging system include an imaging assembly, a table, a table positioner, and a foot-activated controller. The table positioner may interact with the table, while the foot-activated controller is operatively interconnected with each of the imaging assembly and the table positioner. The foot-activated controller includes at least one actuator, including at least one first actuator and at least one second actuator. Each first actuator is dedicated to communicating with the imaging assembly. Each second actuator is dedicated to communicating with the table positioner.

A second aspect of the present invention is embodied by an imaging system. Components of this imaging system include an imaging assembly, a table, a table positioner, and a foot-activated controller. The table positioner may interact with the table, while the foot-activated controller is operatively interconnected with each of the imaging assembly and the table positioner. The foot-activated controller includes first and second controller sections that may be selectively joined and separated. Each of the first and second controller sections includes at least one actuator, and each such actuator communicates with at least one of the imaging assembly and the table positioner.

Various refinements exist of the features noted in relation to the second aspect of the present invention. Further features may also be incorporated in the second aspect of the present invention as well. These refinements and additional features may exist individually or in any combination. The foot-activated controller may include at least one first actuator and at least one second actuator. Each first actuator may be dedicated to communicating with the imaging assembly (e.g., one or more components that are directed to the acquisition of an image). Each second actuator may be dedicated to communicating with the table positioner.

Various refinements exist of the features noted in relation to each of the above-noted first and second aspects of the present invention. Further features may also be incorporated in each of the above-noted first and second aspects of the present invention as well. These refinements and additional features may exist individually or in any combination in relation to each of the first and second aspects. That is, each of the following features that will be discussed is not required to be used with any other feature or combination of features unless otherwise specified.

The imaging system may be utilized for any appropriate application. In one embodiment, the imaging system is used for a medical application (e.g., for performing one or more urology procedures), and thereby may be referred to as a medical imaging system. Any appropriate imaging equipment may be utilized by the imaging system, including without limitation one or more components for providing an imaging functionality such as x-ray, tomography, fluoroscopy, store last image hold, magnification, and any combination thereof.

The table may be movable in any appropriate manner and/or in any appropriate dimension or combination of dimensions. The table may be moved in each of first and second directions within a reference plane that at least generally coincides with a supporting surface of the table. These two different directions may be orthogonal to each other—for instance one defining a longitudinal dimension or longitudinal axis (e.g., coinciding with a height dimension of a patient lying on the table, or coinciding with a dimension in which the patient's head and feet are spaced when lying on the table) and the other defining a lateral dimension or axis (e.g., coinciding with a dimension in which a patient's shoulders would be spaced if the patient were to lie on his/her back on the table in the above-noted manner). The longitudinal dimension or axis may coincide with the long axis of the supporting surface of the table, while the lateral dimension or axis may coincide with the short axis of the supporting surface of the table.

Another motion that the table may undergo is in the vertical dimension—a motion that changes the elevation of the table (and including the entirety of its supporting surface). Yet another type of motion that may be utilized for the table is a movement at least generally about a first axis. This first axis is subject to a number of characterizations, which apply individually and in any appropriate combination. For instance, the first axis may be horizontally disposed, may extend in the lateral dimension, or both. In one embodiment, the lateral dimension of the supporting surface of the table is maintained parallel to horizontal. Movement of the table at least generally about the first axis may be characterized as a tilting of the table. The angle at which the table is disposed relative to horizontal (e.g., the angle between the longitudinal axis of the table and horizontal) may be referred to as a "tilt angle."

Tilting of the table may be undertaken to raise the patient's head and simultaneously lower the patient's feet, may be undertaken to lower the patient's head and simultaneously raise the patients feet, or both.

At least four first actuators may be utilized by the foot-activated controller. One first actuator may be utilized to control x-ray imaging (e.g., dedicated to controlling the acquisition of an x-ray image, for instance by turning on/off x-ray equipment); one first actuator may be utilized to control fluoroscopy imaging (e.g., dedicated to controlling the acquisition of a fluoroscopy image, for instance by turning on/off fluoroscopy equipment); one first actuator may be used to establish/select the magnification mode of an image to be acquired; and one first actuator may be used to control the saving of an image to be acquired (e.g., to turn on/off an image saving function). Each first actuator may be of any appropriate size, shape, configuration, and/or type, for instance in the form of an on/off switch.

At least two second actuators may be utilized by the foot-activated controller. One first actuator may be utilized to control movement of the table in each of the above-noted first and second directions (e.g., each being within a reference plane that coincides with a supporting surface of the table). Another first actuator may be utilized to both control movement of the table in the vertical dimension and to control the above-noted tilt angle of the table (e.g., the angle between horizontal and the longitudinal axis of the table supporting surface). Each second actuator may be of any appropriate size, shape, configuration, and/or type, for instance in the form of a four-position switch.

The foot-activated controller may include at least one third actuator. This third actuator may be dedicated to communicating with and controlling movement of at least a portion of the imaging assembly. In one embodiment, a single third actuator is used by the foot-activated controller, and this third actuator is used to control the movement of what may be referred to as an "imaging chain" of the imaging assembly (e.g., an x-ray tube and associated receiver).

The arrangement of the first and second actuators is subject to a number of characterizations, which apply individually and in any combination. Each second actuator (e.g., its actuating surface) may be disposed at a higher elevation than each first actuator (e.g., its actuating surface). The foot-activated controller may include first and second controller sections, with each first actuator being incorporated by the first controller section, and with each second actuator being incorporated by the second controller section. In one embodiment, the second controller section defines an upper level of the foot-activated controller when the first and second controller sections are in a joined or coupled state, while the first controller section defines a lower level of the foot-activated controller when the first and second controller sections are in a joined or coupled state.

The first and second controller sections are subject to a number of characterizations, which apply individually and in any combination. The first and second controller sections may be characterized as being detachably interconnected. Another characterization is that the first and second controller sections may be interlocked (e.g., selectively). Yet another characterization is that the first and second controller sections may be placed or configured in each of a joined state and a separated state. In one embodiment, each actuator utilized by each of the first and second controller sections is operable when the first and second controller sections are in a joined or coupled state, as well as when in a separated or uncoupled state. Therefore, the foot-activated controller may be used in either of these two general configurations. Whether the first and second controller sections are characterized as being detachably interconnected, interlocked, or in a joined or coupled state, the first and second controller sections in this type of configuration may be moved collectively along a floor on which the foot-activated controller is disposed. Otherwise, the first and second controller sections may be moved independent of each other to at least some extent.

One or more communication links of any appropriate type may exist between each actuator utilized by the foot-activated controller and a corresponding one of the imaging assembly and the table positioner. In one embodiment, at least one wireless communication link between the foot-activated controller and at least one of the imaging assembly and the table positioner is in the form of a wireless communication link. For instance, the above-noted first controller section may wirelessly communicate with the imaging assembly, while the above-noted second controller section may wirelessly communicate with the table positioner. Each "command" that is sent by an actuator to a corresponding one of the imaging assembly and the table positioner may be associated with a particular identifier. This identifier may be unique to one of a plurality of the imaging systems encompassed by the present invention. Therefore and in the case that a plurality of imaging systems are being operated in proximity to one another, each actuator from each of the foot-activated controllers should only be able to wirelessly communicate with the imaging assembly and/or table positioner of its corresponding imaging system. Wireless methods can be radio frequency (RF) type such as Bluetooth® and ZigBee®, light-based such as infrared, or sound-based (preferably in the inaudible range such as ultrasound).

One or more alarms may be utilized by the imaging system. The foot-activated controller may include one or more range alarms of any appropriate size, shape, configuration, and/or type (e.g., a visual/optical alarm, an audible alarm). Generally, a range alarm may be activated when a corresponding foot-activated controller (or a corresponding portion thereof) has reached and/or exceeded the range of a corresponding wireless communication link. Wireless methods can be RF type such as Bluetooth® and ZigBee®, light-based such as infrared, or sound-based (preferably in the inaudible range such as ultrasound). The foot-activated controller may include one or more locating alarms of any appropriate size, shape, configuration, and/or type (e.g., a visual/optical alarm, an audible alarm). Generally, a locating alarm may be activated in any appropriate manner (e.g., by manual activation of a locating switch or the like at an appropriate location, such as on the patient table), and may be used to find the corresponding foot-activated controller (or a corresponding portion thereof). Each of the above-noted first and second controller sections could include a range alarm, a locating alarm, or both.

A third aspect of the present invention is embodied by a method for operating an imaging system. This imaging system includes a table, a table positioner, and an imaging assembly. First and second controller sections may be joined together or may be separated from each other. The first controller section includes at least one first actuator, while the second controller section includes at least one second actuator. The first and second actuators may be operated to control at least one aspect of the imaging assembly and table positioner, respectively, including when the first and second controller sections are in a joined or coupled state and when the first and second controller sections are in a separated or uncoupled state.

A fourth aspect of the present invention is embodied by a method of operation for an imaging system. This imaging system includes a table, a table positioner, an imaging assembly, and first and second controller sections. The first controller section includes at least one first actuator, while the second controller section includes at least one second actuator. A signal is sent from at least one first actuator to the imaging assembly when the first and second controller sections are in a joined or coupled state, and another signal is sent from at least one first actuator to the imaging assembly when the first and second controller sections are in a separated or uncoupled state. A signal is sent from at least one second actuator to the table positioner when the first and second controller sections are in a joined or coupled state, and another signal is sent from at least one second actuator to the table positioner when the first and second controller sections are in a separated or uncoupled state.

Various refinements exist of the features noted in relation to each of the above-noted third and fourth aspects of the present invention. Further features may also be incorporated in each of the above-noted third and fourth aspects of the present invention as well. These refinements and additional features may exist individually or in any combination in relation to each of the third and fourth aspects. That is, each of the following features that will be discussed are not required to be used with any other feature or combination of features unless otherwise specified. Each of the third and fourth aspects may utilize the imaging system of each of the first and second aspects.

DETAILED DESCRIPTION

Figure 1:
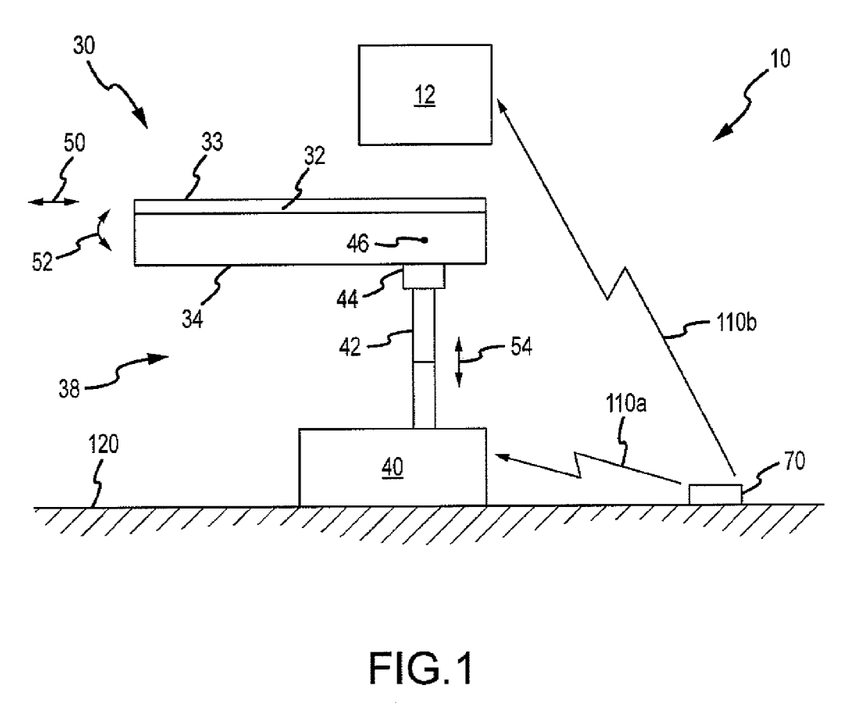
FIG. 1 is a schematic of one embodiment of an imaging system that uses a foot-activated controller.

One embodiment of an imaging system is illustrated in FIG. 1 and is identified by reference numeral 10. The imaging system 10 may be used for any appropriate application, including without limitation a medical application. Therefore, the imaging system 10 may be referred to as a medical imaging system 10.

The medical imaging system 10 includes an imaging assembly 12 and a table assembly 30, each of which may be of any appropriate size, shape, configuration, and/or type. The imaging assembly 12 may include any appropriate imaging equipment and any related components (e.g., for providing an x-ray functionality (e.g., acquiring an x-ray image), for providing a tomography functionality (e.g., acquiring a tomography image), for providing a fluoroscopy functionality (e.g., acquiring a fluoroscopy image), store last image hold, magnification, and any combination thereof). Although the medical imaging system 10 may be configured for any appropriate medical application, in one embodiment the medical imaging system 10 is adapted for performing/facilitating the performance of one or more urology procedures.

The table assembly 30 may include a table or a tabletop 32, a table tub 34, and a table positioner 38. The table 32 may be moved relative to the table tub 34 by the table positioner 38 in each of first and second directions within a reference plane that at least generally coincides with a supporting surface 33 of the table 32. Double-headed arrow 50 in FIG. 1 represents one direction in which the table 32 may be moved relative to the table tub 34 within this reference plane, and which may define a longitudinal dimension or axis (e.g., coinciding with or defining the long axis of the supporting surface 33 of the table 32). The table 32 may also be moved relative to the table tub 34 in a direction that is orthogonal to the view presented in FIG. 1, and which may define a lateral dimension (e.g., see FIG. 2, which includes one double-headed arrow 50 to define the longitudinal dimension or axis, and which includes another double-headed arrow 50 to define the lateral dimension or axis). A patient would typically lie head-to-toe in the longitudinal dimension on the supporting surface 33 of the table 32. If the patient were lying on his/her back in this fashion, the patient's shoulders would be spaced in the lateral dimension.

The table positioner 38 may provide multiple movements or movement types for the table 32. The table positioner 38 may be configured to move the table 32 relative to the table tub 34 in the above-noted manner (e.g., in each of the longitudinal and lateral dimensions). The table positioner 38 may be configured to collectively move the table 32 and the table tub 34 in the vertical dimension, and as indicated by the double-headed arrow 54 (e.g., up and down relative to a floor 120, which may support one or more components of the medical imaging system 10). The table positioner 38 may be configured to collectively move the table 32 and the table tub 34 at least generally about an axis 46 that extends in the lateral dimension, that is horizontally disposed, or both, and as indicated by the double-headed arrow 52. This type of motion may be characterized as changing an angle between horizontal and the longitudinal dimension or axis of the supporting surface 33 of the table 32. Another characterization of this motion is that it is a "tilting" the table 52, for instance a "longitudinal tilting" of the table 32 (e.g., raising the head and simultaneously lowering the feet of the patient; lowering the head and simultaneously raising the feet of the patient). Therefore, the axis 46 may be referred to as a "tilt axis 46." The tilt axis 46 may be disposed at any appropriate location in the vertical dimension and at any appropriate location in the longitudinal dimension of the table 32.

The table positioner 38 may be of any appropriate size, shape, configuration, and/or type to move the table 32 in any desired manner. In the illustrated embodiment, the table positioner 38 includes a base 40 that is disposed on the floor 120. The table positioner 38 utilizes a column 42 (e.g., the shaft of an appropriate cylinder) that may be both extended and retracted to raise and lower, respectively, the table 32 in the vertical dimension (e.g., to move the table 32 along an axis corresponding with the double-headed arrow 54). A joint 44 of any appropriate type allows the table positioner 38 to move the table 32 at least generally about the tilt axis 46. Part of the table positioner 38 (not shown) may be located within the table tub 34 or otherwise to move the table 32 relative to the table tub 34 in the above-noted longitudinal and lateral dimensions (e.g., in accordance with the two double-headed arrows 50 shown in FIG. 2).

The medical imaging system 10 of FIG. 1 includes a foot-activated controller 70 for controlling one or more aspects of the operation of both the imaging assembly 12 and the table positioner 38. Therefore, the foot-activated controller 70 may be referred to as a multi-function controller. In any case, any appropriate communication link 110a may exist between the foot-activated controller 70 and the table positioner 38. Similarly, any appropriate communication link 110b may exist between the foot-activated controller 70 and the imaging assembly 12. The communication links 110a, 110b may be of a common or different type. In one embodiment each communication link 110a, 110b is a wireless communication link.

Figure 2:
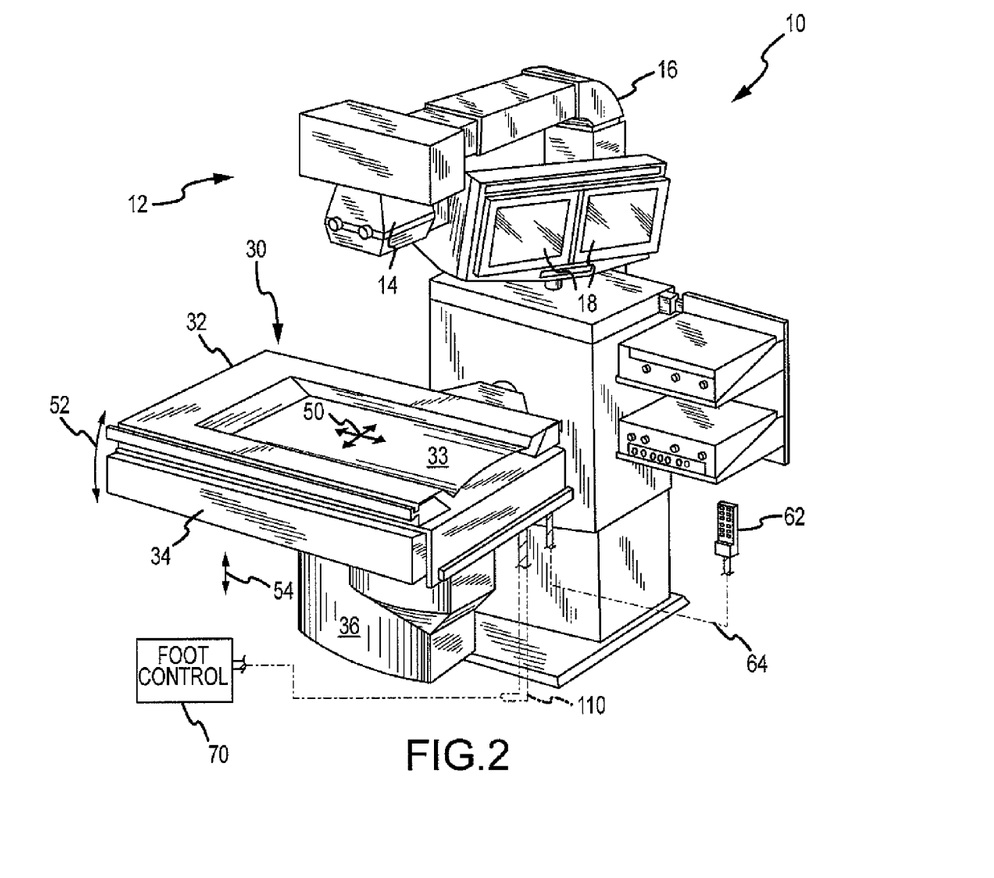
FIG. 2 is a more detailed view (perspective) of the imaging system of FIG. 1.

A more detailed view of the medical imaging system 10 is presented in FIG. 2. Here the imaging assembly 12 includes camera equipment 14 (e.g., for acquiring an x-ray image, for acquiring a tomography image, for acquiring a fluoroscopy image, store last image hold, magnification, and any combination thereof), a support arm 16 for the camera equipment 14, and one or more monitors 18 (two shown) for displaying an acquired image. The lower portion of the table tub 34 is attached to a pedestal 36 in the FIG. 2 configuration. The table positioner 38 is not shown in FIG. 2, but is able to move the table 32 relative to the table tub 34 in each of the longitudinal and lateral dimensions (double-headed arrows 50), is able to collectively move the table 32 and table tub 34 in the vertical dimension (double-headed arrow 54), and is able to collectively and longitudinally tilt the table 32 and table tub 34 at least generally about the tilt axis 46 (double-headed arrow 52).

The foot-activated controller 70 is operatively interconnected with each of the table positioner 38 and the imaging assembly 12 by a communication link 110. In accordance with the foregoing, the communication link 110 may be of any appropriate type (e.g., wireless). Wireless methods can be RF type (e.g., Bluetooth®, Zigbee®), light-based such as infrared, or sound-based (preferably in the inaudible range, such as ultrasound). A separate communication link 110 may be provided between the foot-activated controller 70 and each of the table positioner 38 and the imaging assembly 12 or otherwise. The medical imaging system 10 may also include one or more hand-activated controllers 62, where each such hand-activated controller 62 is operatively interconnected with at least one of the table positioner 38 and the imaging assembly 12 by a communication link 64. Each such communication link 64 may be of any appropriate type (e.g., wireless). A separate communication link 64 may be provided between any particular hand-activated controller 62 and each of the table positioner 38 and the imaging assembly 12 or otherwise. A separate hand-activated controller 62 could also be provided for each of the table positioner 38 and the imaging assembly 12 (not shown).

Figure 3:
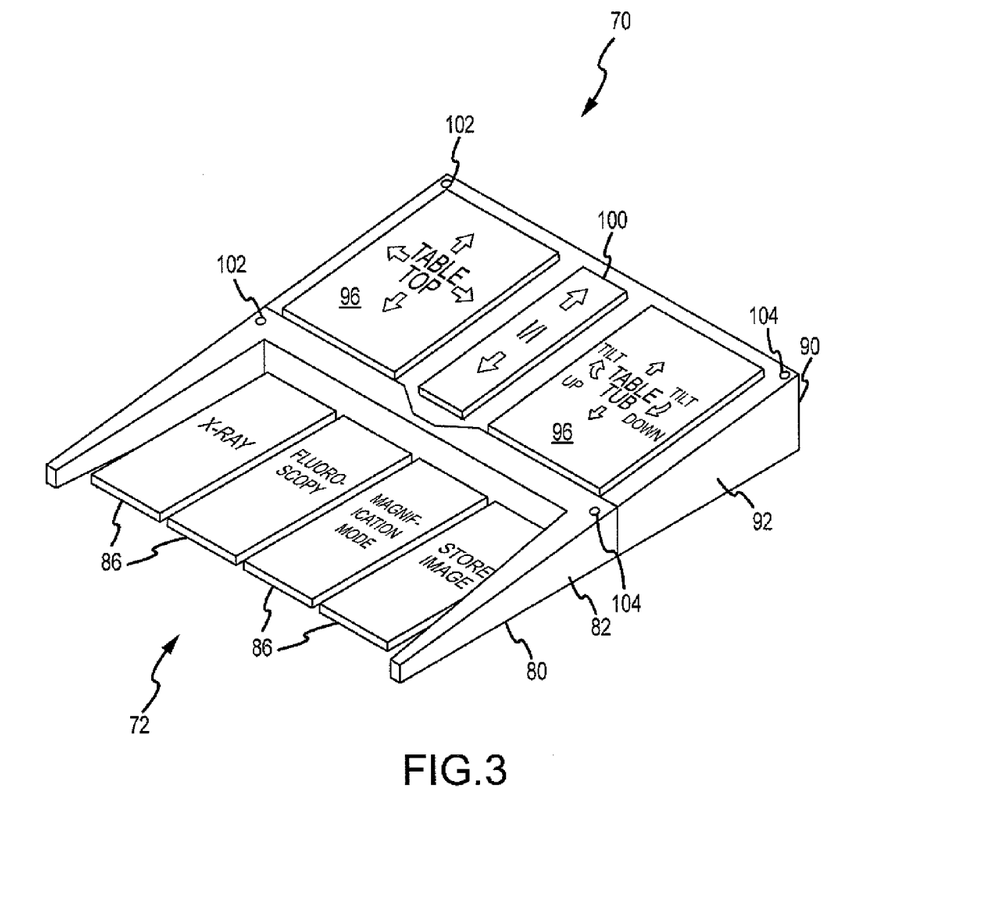
FIG. 3 is a perspective view of a foot-activated controller that may be used by the imaging systems of FIGS. 1 and 2, with its first and second controller sections being in a joined or coupled state.
Figure 4:
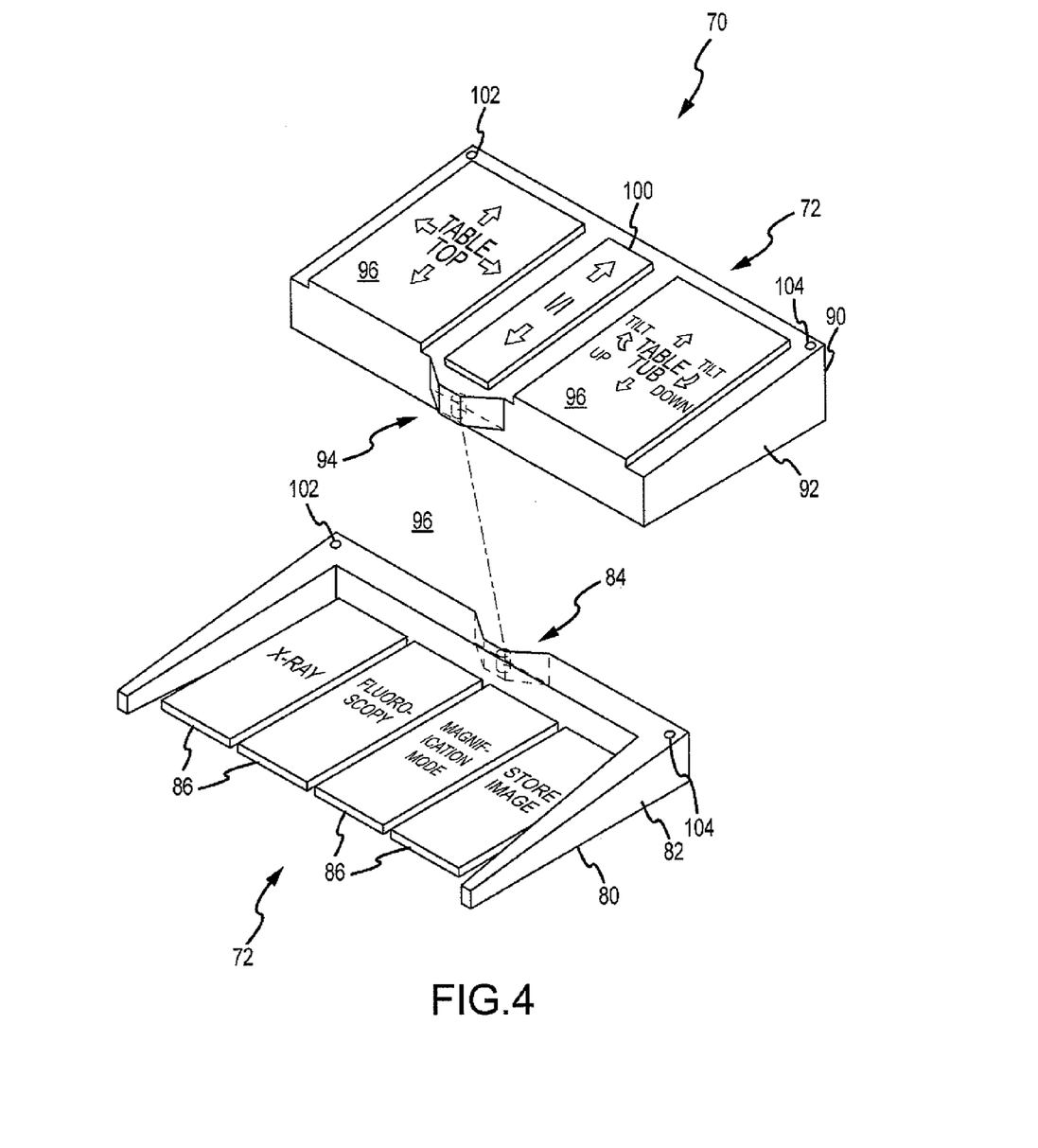
FIG. 4 is a perspective view of the foot-activated controller of FIG. 3, with its first and second controller sections being in a separated or uncoupled state.
Figure 5:
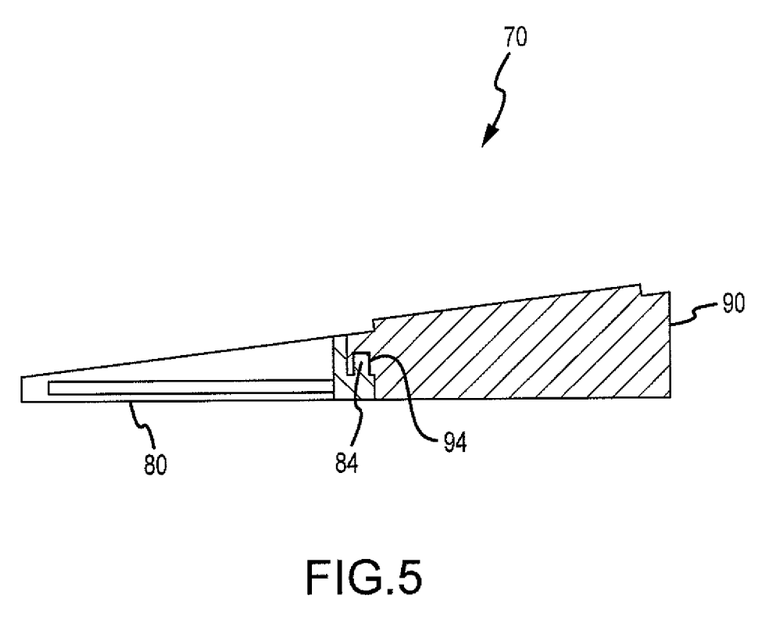
FIG. 5 is a cutaway view of the foot-activated controller of FIG. 3.

One embodiment of the foot-activated controller 70 is illustrated in more detail in FIGS. 3-5. The foot-activated controller 70 includes a first controller section 80 and a second controller section 90, along with at least one actuator 72. Multiple actuators 72 are utilized in the illustrated embodiment, such as at least one first actuator 86, at least one second actuator 96, and at least one third actuator 100. The first controller section 80 includes a first housing 82, while the second controller section 90 includes a second housing 92. The first controller section 80 utilizes at least one first actuator 86, while the second controller section 90 utilizes at least one second actuator 96. In one embodiment, each first actuator 86 is dedicated to communicating with the imaging assembly 12, while each second actuator 96 is dedicated to communicating with the table positioner 38. In one embodiment, all first actuators 86 are integrated with the first controller section 80, while all second actuators 96 are integrated with the second controller section 90.

Any appropriate number of first actuators 86 may be utilized by the first controller section 80, and multiple first actuators 86 may be disposed in any appropriate arrangement. In the illustrated embodiment, one first actuator 86 controls/activates an x-ray functionality (e.g., the acquisition of an x-ray image), another first actuator 86 controls/activates a fluoroscopy functionality (e.g., the acquisition of a fluoroscopy image), another first actuator 86 controls/establishes the selection of a magnification mode for the imaging assembly 12, while another first actuator 86 provides an image saving function. Each first actuator 86 may be of any appropriate size, shape, configuration, and/or type. In one embodiment, each first actuator 86 is in the form of an on/off or two-position switch. Therefore, each first actuator 86 may be characterized as being dedicated to controlling an imaging functionality.

Any appropriate number of second actuators 96 may be utilized by the second controller section 90, and multiple first actuators 96 may be disposed in any appropriate arrangement. In the illustrated embodiment, one second actuator 96 controls both the longitudinal and lateral position of the table 32 relative to the table tub 34 (e.g., to control the movement of the table 32 in the direction of the double-headed arrows 50 shown in FIG. 2), while another second actuator 96 controls both a position of the table 32 in the vertical dimension (e.g., to control the movement of the table 32 in the direction of the double-headed arrow 54 shown in FIG. 2) and the tilt angle of the table 32 (e.g., to control the movement of the table in the direction of the double-headed arrow 52 shown in FIG. 2). Each second actuator 96 may be of any appropriate size, shape, configuration, and/or type. In one embodiment, each second actuator 86 is in the form of a four-position switch. Therefore, each second actuator 96 may be characterized as being dedicated to controlling motion of the table 32.

The foot-activated controller 70 also includes at least one third actuator 100. Any appropriate number of third actuators 100 may be utilized by the foot-activated controller 70. In one embodiment, a single third actuator 100 is incorporated by the second controller section 90 and this third actuator 100 controls the movement of at least part of the imaging assembly 12 (e.g., movement of what may be characterized as an "imaging chain," such as a collective movement of an x-ray tube and receiver). Therefore, each third actuator 100 may be characterized as being dedicated to controlling motion of the imaging assembly 12.

Based upon the foregoing, each actuator 72 utilized by the first controller section 80 (first actuators 86) may be characterized as being dedicated to controlling the acquisition of an image. Each actuator 72 utilized by the second controller section 90 (second actuators 96 and third actuator 100) may be characterized as being dedicated to controlling motion of at least a portion of the medical imaging system 10.

Each of the first housing 82 (first controller section 80) and the second housing 92 (second controller section 90) may be of any appropriate size, shape, configuration, and/or type. The first housing 82 utilizes at least one registration and/or locking member 84, while the second housing 92 utilizes at least one registration and/or locking 94. Each of the first registration/locking member 84 and the second registration/locking member 94 may be of any appropriate size, shape, configuration, and/or type. Each first registration/locking member and each second registration/locking member 94 may be disposed in any appropriate arrangement. Generally, each first registration/locking member 84 may interface with a corresponding second registration/locking member 94 to provide an appropriate physical interconnection between the first controller section 80 and the second controller section 90, to limit relative movement between the first controller section 80 and second controller section 90 in at least one direction or dimension, or both. In one embodiment, the first controller section 80 and second controller section 90 are moved vertically relative to each other to selectively couple/uncouple the same.

The interconnection between the first controller section 80 and the second controller section 90 is subject to a number of characterizations. One is that the first controller section 80 and the second controller section 90 may be characterized as being detachably interconnected. Another is that the first controller section 80 and the second controller section 90 may be characterized as being interlocked (e.g., selectively). Another is that the first controller section 80 and the second controller section 90 may be characterized as being coupled (e.g., selectively). Yet another is that the first controller section 80 and the second controller section 90 may be characterized as being disposable in each of a joined, connected, or coupled state and an un-joined, disconnected, or uncoupled state. When the first controller section 80 and the second controller section 90 are physically interconnected, they may be collectively moved (e.g., along the floor 120). When the first controller section 80 and the second controller section 90 are disconnected, uncoupled, or separated from each other, the first controller section 80 and the second controller section 90 may be moved (e.g., along the floor 120) independent of each other to at least some extent.

The first controller section 80 and the second controller section 90 may be disposed in any appropriate position relative to each other when in a joined or coupled state. In the illustrated embodiment, the second controller section 90 defines an upper level for the foot-activated controller 70 when the first controller section 80 and the second controller section 90 are in a joined/coupled state, while the first controller section 80 defines a Lower level for the foot-activated controller 70 when the first controller section 80 and the second controller section 90 are in a joined/coupled state. Therefore, each second actuator 96 may be characterized as being disposed at a higher elevation than each first actuator 86 when the first controller section 80 and the second controller section 90 are in a joined or coupled state. In one embodiment, the foot-activated controller 70 is at least generally wedge-shaped in a side view (FIG. 5) and when the first controller section 80 and the second controller section 90 are in a joined or coupled state.

Based upon the foregoing, the foot-activated controller 70 may be operated when disposed in each of two different configurations. The first controller section 80 and the second controller section 90 may be joined together or coupled, and an operator (e.g., an attending physician) may independently operate each of the various first actuators 86, each of the various second actuators 96, and each of the various third actuators 100. The foot-activated controller 70 may also be configured such that the first controller section 80 is separated or uncoupled from the second controller section 90, such that the first controller section 80 and the second controller section 90 may be separately positioned to at least some extent, and where an operator (e.g., an attending physician) may independently operate each of the various first actuators 86, each of the various second actuators 96, and each of the various third actuators 100. That is, the first controller section 80 and the second controller section 90 may be characterized as being selectively joined/coupled or separated/uncoupled as desired.

The foot-activated controller 70 may utilize one or more alarms of any appropriate size, shape, configuration, and/or type (e.g., optical, audible). At least one range alarm 102 and at least one locating alarm 104 may be utilized by the foot-activated controller 70. In one embodiment, each of the first controller section 80 and the second controller section 90 incorporates at least one range alarm 102 and at least one locating alarm 104. Each range alarm 102 may be activated when a corresponding portion of the foot-activated controller 70 is located outside of a predetermined range from one or more of the imaging assembly 12 and the table positioner 38. Each locating alarm 104 may be activated by an individual in any appropriate manner (e.g., by incorporating one or more switches at an appropriate location of the medical imaging system 10) in an attempt to locate a corresponding portion of the foot-activated controller 70.

Figure 6:
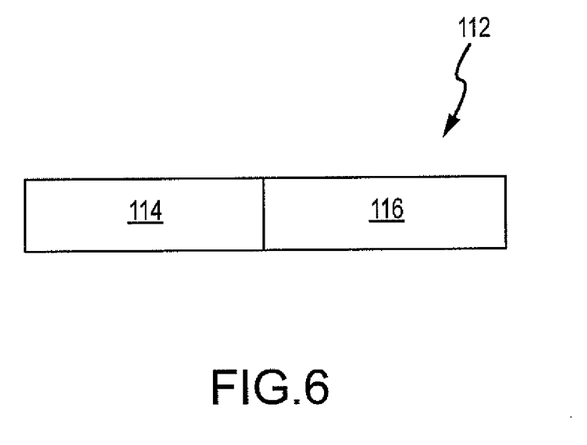
FIG. 6 is a schematic of a representative wireless signal that may be used by the foot-activated controller of FIG. 3.

As noted above, the foot-activated controller 70 may communicate wirelessly with one or both of the imaging assembly 12 and the table positioner 38. In this case, it may be desirable to reduce the potential that the foot-activated controller 70 will communicate with anything other than its associated medical imaging system 10. For instance, consider the case where one medical imaging system 10 is located in one room, and another medical imaging system 10 is located in an adjacent room. Each medical imaging system 10 may be configured to utilize wireless communications in a manner that reduces the potential for the foot-activated controller 70 from one of these medical imaging systems 10 being able to communicate with the imaging assembly 12 and/or table positioner 38 of the other adjacent medical imaging system 10. FIG. 6 illustrates a representative wireless communication for this type of situation.

A wireless signal 112 is illustrated in FIG. 6 and may be characterized as including an identifier segment 114 and a command segment 116. The identifier segment 114 may be unique to one of a plurality of medical imaging systems 10. Therefore, a first medical imaging system 10 would have a different identifier segment 114 than a second medical imaging system 10. Each actuator 72 of one medical imaging system 10 may communicate with the corresponding imaging assembly 12 and/or table positioner 38 by sending one or more wireless signals 112 (e.g., using a common identifier segment 114), whereas each actuator 72 of another medical imaging system 10 may communicate with either its corresponding imaging assembly 12 and/or table positioner 38 by sending one or more wireless signals 112 (e.g., using a different identifier segment 114).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An imaging system, comprising:
   an imaging assembly;
   a table;
   a table positioner that interacts with said table; and
   a controller operatively interconnected with each of said imaging assembly and said table positioner, wherein said controller is foot-activated, wherein said controller comprises at least one actuator, wherein said at least one actuator comprises at least one first actuator and at least one second actuator, wherein each said first actuator is dedicated to controlling an imaging functionality of said imaging assembly such that each said first actuator can only be used to control said imaging functionality of said imaging assembly, wherein each said second actuator is dedicated to controlling motion of said table through said table positioner such that each said second actuator can only be used to control said motion of said table through said table positioner, wherein activation of each said second actuator causes movement of said table through said table positioner, wherein said controller comprises first and second controller sections, wherein each said first actuator is integrated with said first controller section, wherein each said second actuator is integrated with said second controller section, wherein said controller comprises a first configuration where each said actuator of said controller is part of a common structure and where said first and second controller sections are in a coupled state so that said first and second controller sections are collectively movable, wherein said controller comprises a second configuration where said first and second controller sections are in an uncoupled state where said first and second controller sections are uncoupled from one another and are independently movable relative to one another, and wherein each said first actuator and each said second actuator are operable when said first and second controller sections are in each of said coupled state and said uncoupled state.

2. The imaging system of claim 1, wherein said imaging system is adapted for at least a urology application.

3. The imaging system of claim 1, wherein said imaging assembly comprises equipment selected from the group consisting of x-ray, tomography, fluoroscopy, store last image hold, magnification, and any combination thereof.

4. The imaging system of claim 1, wherein said table is movable in first and second directions within a first plane that coincides with a supporting surface of said table, is movable in a vertical dimension, and is tiltable at least generally about a first axis.

5. The imaging system of claim 4, wherein said first axis is at least generally horizontally disposed.

6. The imaging system of claim 1, wherein said at least one actuator comprises at least four said first actuators.

7. The imaging system of claim 6, wherein one said first actuator controls an acquisition of an x-ray image, wherein another said first actuator controls an acquisition of a fluoroscopy image, wherein another said first actuator controls a magnification mode for an image to be acquired, and wherein another said first actuator controls a saving of an image to be acquired.

8. The imaging system of claim 1, wherein each said first actuator comprises an on/off switch.

9. The imaging system of claim 1, wherein said at least one actuator comprises at least two said second actuators.

10. The imaging system of claim 9, wherein one said second actuator controls movement of said table in each of first and second directions within a first plane that coincides with a supporting surface of said table, and wherein another of said second actuators controls both a position of said table in a vertical dimension and a tilt angle of said table relative to a first axis.

11. The imaging system of claim 10, wherein said first axis is at least generally horizontally disposed.

12. The imaging system of claim 1, wherein each said second actuator comprises a four-position switch.

13. The imaging system of claim 1, wherein said controller comprises a third actuator that is dedicated to controlling movement of at least a portion of said imaging assembly.

14. The imaging system of claim 1, wherein each said second actuator is disposed at a higher elevation than each said first actuator.

15. The imaging system of claim 1, wherein an activating surface of each said first actuator is disposed at a common elevation, and wherein an activating surface of each said second actuator is disposed at a common elevation.

16. The imaging system of claim 1, wherein said first and second controller sections comprise first and second registration members, respectively, wherein when said first registration member of said first controller section interfaces with said second registration member of said second controller section relative movement between said first and second controller sections is limited in at least one direction.

17. The imaging system of claim 1, wherein said first and second controller sections are detachably interconnected.

18. The imaging system of claim 1, wherein said first controller section may be selectively interlocked with said second controller section.

19. The imaging system of claim 1, wherein said first controller section is moved vertically relative to said second controller section to selectively couple said first and second controller sections and to selectively uncouple said first and second controller sections.

20. The imaging system of claim 1, wherein said first and second controller sections collectively define a wedge-shaped structure in a side view and when in said coupled state.

21. The imaging system of claim 1, wherein said second controller section defines an upper level of said controller when said first and second controller sections are in said coupled state, and wherein said first controller section defines a lower level of said controller when said first and second controller sections are in said coupled state.

22. The imaging system of claim 1, wherein said first and second controller sections comprise first and second housings, respectively.

23. The imaging system of claim 1, further comprising a communications link between each said actuator and at least one of said imaging assembly and said table positioner, wherein each of said communications links comprises a wireless communication link.

24. The imaging system of claim 23, wherein said wireless communications link is selected from the group consisting of radio frequency, light-based, and sound-based.

25. The imaging system of claim 23, wherein each signal transmitted by each said actuator comprises an identifier segment and a command segment.

26. The imaging system of claim 25, wherein said identifier segment is unique to one of a plurality of said imaging systems.

27. The imaging system of claim 23, further comprising at least one range alarm that is activated when any said actuator is located outside of a predetermined range from a corresponding one of said imaging assembly and said table positioner.

28. The imaging system of claim 1, wherein said controller comprises a locating alarm, and wherein said imaging system comprises a locating switch for selectively activating said locating alarm.

29. An imaging system, comprising:
an imaging assembly;
a table;
a table positioner that interacts with said table; and a controller operatively interconnected with each of said imaging assembly and said table positioner, wherein said controller is foot-activated, wherein said controller comprises at least one actuator, wherein said at least one actuator comprises at least one first actuator and at least one second actuator, wherein each said first actuator is dedicated to controlling an imaging functionality of said imaging assembly such that each said first actuator can only be used to control said imaging functionality of said imaging assembly, wherein each said second actuator is dedicated to controlling motion of said table through said table positioner such that each said second actuator can only be used to control said motion of said table through said table positioner, wherein activation of each said second actuator causes movement of said table through said table positioner, and wherein said controller comprises a first configuration where each said actuator of said controller is part of a common structure.

* * * * *